United States Patent [19]

Verrando, III

[11] Patent Number: 4,882,648

[45] Date of Patent: Nov. 21, 1989

[54] CAPACITANCE PROBE FOR USE IN ABSORBENT SYSTEMS

[75] Inventor: Marcel G. Verrando, III, Ocala, Fla.

[73] Assignee: Pall Corporation, East Hills, N.Y.

[21] Appl. No.: 255,667

[22] Filed: Oct. 11, 1988

[51] Int. Cl.[4] .................. H01G 5/00; G01R 27/26; B01D 53/04

[52] U.S. Cl. .................................. 361/286; 55/33; 324/61 R

[58] Field of Search ............... 361/286; 73/73; 324/61 R; 55/18, 20, 33

[56] References Cited

U.S. PATENT DOCUMENTS

| | | | |
|---|---|---|---|
| 2,703,628 | 3/1955 | Pompeo et al. | 183/4.1 |
| 4,322,223 | 3/1982 | Christel | 55/33 X |
| 4,549,134 | 10/1985 | Weiss | 324/61 R |
| 4,552,570 | 11/1985 | Gravatt | 55/33 X |
| 4,664,683 | 5/1987 | Degen et al. | 55/387 |
| 4,752,855 | 6/1988 | Fedter et al. | 361/286 |

Primary Examiner—Donald Griffin
Attorney, Agent, or Firm—Leydig, Voit & Mayer

[57] ABSTRACT

A capacitance probe having a relative thin profile and large cross section for use in short yet relatively large diameter desiccant beds is formed from two substantially identical members, each having a network of strip elements electrically and structurally connecting a plurality of plate elements. Upon inverting and rotating one member with respect to the other member, the plate elements of one member are interleaved with the plate elements of the other while leaving enough space to accommodate a sufficient volume of sorbent to serve as the dielectric. The probe may be employed with supporting circuitry to detect the advance of the moisture front as a change in dielectric constant of the sorbent. There is also provided a system to connect the two members in nonconducting relation so that a rigid structure results.

11 Claims, 1 Drawing Sheet

CAPACITANCE PROBE FOR USE IN ABSORBENT SYSTEMS

FIELD OF THE INVENTION

This invention relates generally to capacitor designs and more particularly concerns a capacitor probe for use in adsorbent systems to sense the moisture front in an adsorbent bed during adsorption, regeneration, or both.

BACKGROUND

Detecting the advance of the moisture front in a bed of sorbent by determining the change in the moisture content of the sorbent as a function of a capacitor in which the sorbent is the dialectric is known in the art and described in U.S. Pat. No. 2,703,628 to Pompeo et al. and in U.S. Pat. No. 4,552,570, patented Nov. 12, 1985 to Gravatt, the latter being commonly assigned and incorporated herein by reference.

Typical commercial driers in use today employ two desiccant chambers, each approximately six feet long, ten inches in diameter, and weighing about six hundred pounds. Capacitance probes used in these large drier chambers generally have taken the form of a series of alternately connected circular discs, about two inches in diameter and 1/16 inch thick. In order to accommodate a sufficient volume of sorbent between each disc to detect the change in dielectric of the sorbent as the moisture level within the sorbent bed increases, the discs are spaced ½ inch apart, such that a capacitor with ten discs has a generally cylindrical shape about six inches long and two inches in diameter. This unit is placed transversely in the desiccant bed with respect to the gas flow to detect the moisture front.

Unlike large, commercial driers, adsorbent fractionators for some applications such as those disclosed in U.S. application Ser. No. 736,479 filed May 21, 1985 as well as such specialized applications as avionics cooling, macro and micro-personnel cooling, and purifying air for breathing in fixed wing and rotary wing aircraft, watercraft, hospitals, and the like often necessitate stringent weight and size requirements. For example, in order to meet size specifications for certain aircraft applications, the desiccant beds may need to be as short as about 0.4 to 0.6 feet long and have anywhere between four and sixteen inch diameter chambers, resulting in a small chamber that, even filled with adsorbent particles, weighs only about fifty pounds.

It has been appreciated that the capacitor design described above is not a mechanically acceptable design for this configuration of bed. This is because the capacitor should not only sample a relatively thin section of desiccant to accurately sense the location of the moisture front but should also sample a large fraction of the cross section of the bed to assure a representative reading. An improved design for short, yet relatively large diameter bed adsorption systems is necessary.

SUMMARY OF THE INVENTION

It is an object of the present invention to provide a capacitance probe for use in short yet relatively large diameter adsorbent beds.

It is a related object of the present invention to provide a capacitance probe that is a small fraction of the length of a short yet relatively large diameter adsorbent bed while sampling a large fraction of the cross-sectional area of such a bed.

It is a further object of the present invention to provide a capacitance probe which encompasses a relatively large volume of desiccant while presenting minimal disruption of gas flow through the bed.

These objects and advantages are accomplished in the present invention which provides for a relatively thin, large cross section capacitance probe. In one embodiment the probe is formed from two pieces of sheet materials, each configured to a network of strip elements connecting a plurality of plate elements. In a preferred embodiment, substantially identical members are produced in a flat configuration and the plate elements are thereafter bent 90° to the plane of the member. One member is inverted and rotated with respect to the second member so that the plate elements of one member are interposed between the plate elements of the other member. Additionally, there is provided a system for interlocking, in an insulating relation, at least some of the plate elements of one member with the strip elements of the other member so that a rigid structure results. The structure formed can encompass a relatively large volume of desiccant while presenting a streamlined cross section for minimal disruption of gas flow through the bed.

In the preferred embodiment, the two members are configured to be hexagonal and the plate elements are relatively short, thereby making the assembled capacitance probe relatively thin with respect to the length of the desiccant bed while occupying a substantial portion of the cross-sectional area of the bed. The probe is particularly suited for sensing the moisture front in a relatively short desiccant bed.

BRIEF DESCRIPTION OF THE DRAWINGS

Other objects and advantages will become apparent from the attached detailed description and upon reference to the drawings, in which.

DETAILED DESCRIPTION OF THE PREFERRED EMBODIMENT

While the invention will be described in connection with a preferred embodiment, it will be understood that there is no intention to limit the invention to that embodiment. On the contrary, it is intended to cover all alternatives, modifications and equivalents as may be included within the spirit and scope of the invention as defined by the appended claims.

Turning now to the drawings, a desiccant chamber 11 is shown housing a bed of sorbent material 13. Desiccant chamber 11 shown is of the type adapted for use in aircraft applications requiring adsorbent fractionators having short yet relatively large diameter beds. For such applications, each desiccant chamber 11 can be as short as approximately six inches long, and have a diameter ranging from about four inches to about sixteen inches.

Figure 1:
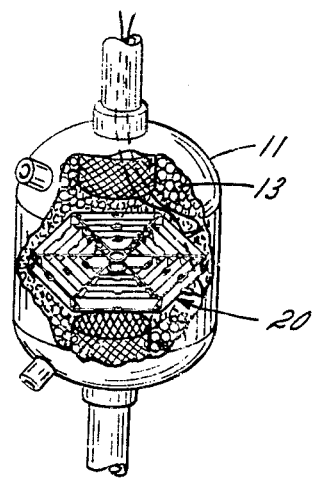
FIG. 1 is a desiccant chamber with a capacitance probe according to the present invention placed therein.

As shown in FIG. 1, within chamber 11 there is positioned a capacitance probe generally indicated at 20. Although illustrated about one-half way along the length of chamber 11, it will be appreciated that capacitance probe 20 may be positioned closer to either end of chamber 11 depending upon whether the moisture front to be detected occurs during the adsorption phase or the regeneration phase of the fractionator. Considerations on the location of the capacitance probe are discussed in Gravatt U.S. Pat. No. 4,552,570 noted above. It will also be appreciated that multiple capacitance probes may be present in the desiccant chamber 11. For example, a plurality of probes may be spaced along the length of the bed so that the moisture front may be more accurately located at any particular time during the adsorption phase or regeneration phase.

Considering briefly the overall design, the capacitance probe shown is made from two substantially identical members, each having a network of strip elements connecting a plurality of plate elements. The plate elements are either formed or bent 90° to the plane of the strip elements so that, upon inverting and rotating one member with respect to the other, the plate elements of one member are interposed with the plate elements of the other. Additionally, in order to aid in handling and in accurately maintaining the configuration of the capacitance probe once it is installed in the chamber and desiccant bed, there is provided a system of interlocking at least some of the plate elements of one member with at least some of the strip elements of the other member so that a rigid structure results.

Figure 2:
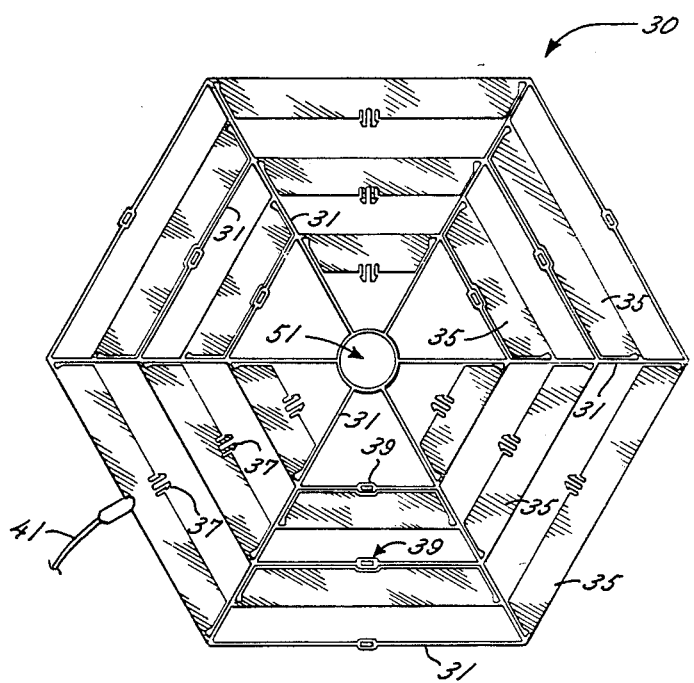
FIG. 2 is a member according to the present invention before the plate elements are bent into their operative positions.
Figure 3:
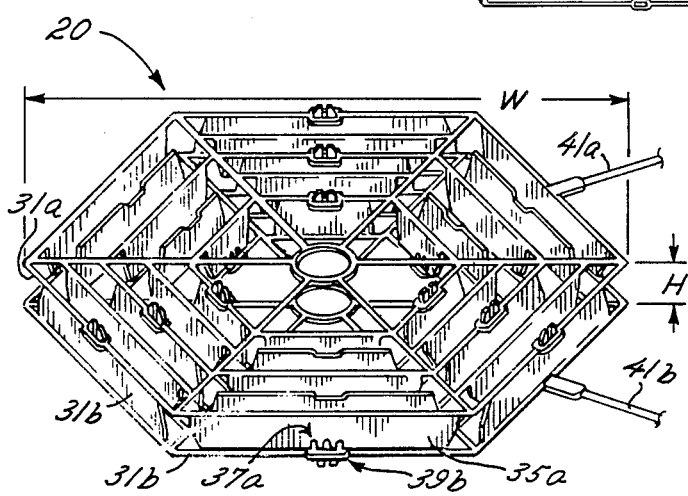
FIG. 3 in an assembled capacitance probe according to the present invention.

Considering the design of the preferred embodiment in greater detail, the assembled capacitance probe 20 shown in FIGS. 1 and 3 is assembled from two members 30. An individual member 30, prior to bending into its final configuration, is shown in FIG. 2. In keeping with an object of the invention, to minimize the impedance to the flow of gas, the material from which each member 30 is made should be relatively thin. One suitable material is aluminum about 0.015 inches thick. This material is suitable for photo etching to achieve the final configuration described in more detail below. As will be appreciated by those skilled in the art, however, member 30 may be formed in a number of suitable ways, including laser cutting or chemical etching, and from alternate suitable materials such as stainless steel.

As will also be appreciated by those skilled in the art, as gas flows from one end of the desiccant bed to the other during the adsorption phase, the adsorption may not occur completely uniformly across the cross section of the bed. Typically, the moisture front may advance more rapidly in the center core of the bed than along the periphery. Therefore, in order to more accurately determine the remaining adsorption capacity of the bed, a capacitance probe able to detect the moisture content of the adsorbent across a relatively large cross section of the bed is desirable.

In the illustrated embodiment, member 30 is a regular hexagon having six sections, each generally an equilateral triangle in shape. Although this shape has been found to provide good capacitive sensing ability across a substantial cross-sectional area of the desiccant bed, other shapes such as octagonal, square, circular, etc., may be substituted and still remain within the scope of the invention.

Referring to FIG. 2, it will be seen that each triangular portion of member 30 is formed with a plurality of spaced plate elements 35 structurally and electrically connected with a network of strip elements 31. In the embodiment shown, the plate elements 35 are formed such that when bent into their final positions (by hand or by automated equipment such as a progressive die) they will be spaced about one-half inch apart within each triangular section. This spacing can vary from application to application and is primarily dependent upon the size of the desiccant particles used. A probe of the type illustrated has been found to be particularly suitable for use with particles between 200 and 2000 microns, which optionally may be immobilized using the proces described in U.S. Pat. No. 4,664,683 to Degen et al. assigned to the present assignee. The plate elements 35 are laid out such that they are staggered between the adjacent triangular sections for symmetry. Thus, upon inverting and rotating one member with respect to another, the plate elements 35 of each member 30 are interposed with one another. As shown in FIG. 1, in the final assembly the plate elements 35 are parallel to the flow of gas through the desiccant chamber 11. Moreover, it will be seen that in the final assembly the strip elements are aligned with the edges of the plate elements to further minimize flow distribution.

It will be appreciated that the height of the plates in the final assembly should be such that a sufficient volume of desiccant is encompassed by the capacitor to obtain an accurate reading of the content of the desiccant without representing such a significant length of the bed as to impair the ability of the probe to accurately pinpoint the location of the moisture front. An actual prototype of the embodiment shown has been constructed having a tip-to-tip width of about 4 inches, yielding a height (H) of about one-quarter of an inch, yielding a width to height ratio of about 14 to 1.

In keeping with another aspect of the invention, the capacitance probe 20 as shown is provided with a system for interlocking at least some of the plate elements of one member with at least some of the strip elements of the other member so that a substantially rigid structure results. Specifically, strip elements 31 are shown provided with slots 39, which, upon the inverting and rotating process described above, align with and receive clips 37. In order to electrically insulate the two members 30 from one another, and from the sorbent, the members 30 may be anodized, Martin Hard Coated, or insulated using any other suitable insulating process. Thus, clips 37 may be inserted in slots 39 without an electrical connection therebetween to form a rigid capacitance probe which can withstand handling and the packing and compacting of desiccant once the probe is placed in the desiccant chamber 30.

It is noted that in the embodiment shown, members 30 are each provided with central bore 51 formed from strip elements 31 in order to accommodate a central tie rod (not shown) often found along the central core of desiccant beds.

I claim as my invention:

1. A capacitor for use in sensing variations in the dielectric constant of a bed of particles comprising:
   a first member having a plurality of flat plate elements interconnected by a network of strip elements;
   the plate elements being oriented substantially parallel to a common axis;
   the strip elements being oriented substantially perpendicular to the common axis;
   a second member of substantially the same configuration as the first member, the second member being inverted and rotated relative to the first member so that the plate elements of the first member are interposed between the plate elements of the second member and the plate elements of each member align with at least some of the strip elements of the other member; and at least some of the plate elements of the first member interlocking with at least some of the strip elements of the second member in nonconducting electrical contact whereby a substantially rigid structure is formed.

2. A capacitor as defined in claim 1 wherein said first and second members are substantially hexagonal in shape.

3. A capacitor as defined in claim 2 wherein said plate elements are spaced in each member sufficiently to define a space sized to accommodate a volume of sorbent as the dielectric between adjacent interposed plate elements, whereby the capacitor can sense a change in the dielectric constant of said particles between the plates.

4. A capacitor as defined in claim 1 wherein the effective diameter-to-height ratio of the capacitor is approximately 14 to 1.

5. A capacitor as defined in claim 1 wherein said plate elements are coated with an electrically insulating layer so that the capacitor is electrically isolated from the sorbent.

6. A capacitor as defined in claim 5 wherein said sheet conductors are anodized.

7. A capacitor as defined in claim 5 wherein said sheet capacitors are Martin Hard Coated.

8. A capacitor as defined in claim 1 wherein said first and second members are formed from photoetched thin aluminum sheets.

9. A capacitor as defined in claim 1 wherein said first and second members are formed from laser cut aluminum sheets.

10. A capacitor as defined in claim 1 wherein said members are formed from stainless steel.

11. An apparatus for reducing the concentration of a first gas in a mixture thereof with a second gas to below a limiting maximum concentration thereof in the second gas, said apparatus comprising, in combination:

a chamber;

a bed of sorbent within the chamber, said sorbent having a preferential affinity for the first gas, said chamber being relatively short and having a relatively large diameter;

a capacitor probe comprising a first member having a plurality of flat plate elements interconnected by a network of strip elements, the plate elements being oriented substantially parallel to a common axis, the strip elements being oriented substantially perpendicular to the common axis, a second member of substantially the same configuration as the first member, the second member being inverted and rotated relative to the first member so that the plate elements of the first member are interposed between the plate elements of the second member and the plate elements of each member align with at least some of the strip elements of the other member, and at least some of the plate elements of the first member interlocking with at least some of the strip elements of the second member in nonconducting electrical contact whereby a substantially rigid structure is formed, said capacitor probe having a height which is a relatively small fraction of the length of the bed of sorbent and having an effective diameter substantially the same as the diameter of the bed, said sorbent being the dielectric of said capacitor probe and having a dielectric constant which varies as a fraction of the amount of said first gas adsorbed; and a means for detecting a change in the dielectric constant of the sorbent.

* * * * *